US010453558B2

(12) United States Patent
Yang (10) Patent No.: US 10,453,558 B2
(45) Date of Patent: Oct. 22, 2019

(54) METHOD FOR CONSTRUCTING QUADRANTS WITH MULTIPLE INDEPENDENT BIOMARKERS FOR DIAGNOSING NEURODEGENERATIVE DISEASES

(71) Applicant: MagQu Co. LTD., New Taipei (TW)

(72) Inventor: Shieh-Yueh Yang, New Taipei (TW)

(73) Assignee: MAGQU CO. LTD., New Taipei (TW)

( * ) Notice: Subject to any disclaimer, the term of this patent is extended or adjusted under 35 U.S.C. 154(b) by 266 days.

(21) Appl. No.: 15/135,540

(22) Filed: Apr. 21, 2016

(65) Prior Publication Data

US 2017/0004255 A1  Jan. 5, 2017

Related U.S. Application Data

(60) Provisional application No. 62/188,629, filed on Jul. 4, 2015.

(51) Int. Cl.
*G06F 19/00* (2018.01)
*G16B 45/00* (2019.01)

(52) U.S. Cl.
CPC .................. *G16B 45/00* (2019.02)

(58) Field of Classification Search
CPC .......... G06F 19/22; G06F 19/18; G06F 19/12; G06F 19/24; G06F 19/16; G06F 19/34; G06F 19/20; G06F 19/26; G06F 19/3437; G06F 19/36; G06F 19/00; G06F 17/3053; G06F 17/16; G06F 17/18; G06F 16/3347; G06F 16/35; G06F 16/353; G06F 19/30; G06F 16/61; G06F 17/17; G01N 2800/50; G01N 2800/60; G01N 33/6893;

(Continued)

(56) References Cited

U.S. PATENT DOCUMENTS

2012/0303381 A1* 11/2012 Bessette .................. A61B 5/00
705/2

OTHER PUBLICATIONS

López-Cruz P.L., Bielza C., Larrañaga P. (2011) The von Mises Naive Bayes Classifier for Angular Data. In: Lozano J.A., Gámez J.A., Moreno J.A. (eds) Advances in Artificial Intelligence. CAEPIA 2011. Lecture Notes in Computer Science, vol. 7023. Springer, Berlin, Heidelberg.*

(Continued)

*Primary Examiner* — Mary K Zeman
(74) *Attorney, Agent, or Firm* — Hannah Tien (57) ABSTRACT

The present invention relates to a method for constructing quadrants corresponding to different diseases in a frame of concentrations of multiple independent biomarkers, comprising:
(a) transferring original distributed concentrations of every independent biomarker to modified distributed concentrations, comprising:
calculating the mean value and the standard deviation of the original distributed concentrations for a given independent biomarker;
individually subtracting all the original distributed concentrations by the mean value for the given independent biomarker; and
individually dividing all the differences by the standard deviation to get the modified distributed concentrations for the given independent biomarker;
(b) positing the modified distributed concentrations in a frame of multiple independent biomarkers; and
(c) finding a boundary optimally separating neighboring quadrants corresponding to different diseases.

6 Claims, 13 Drawing Sheets

(58) Field of Classification Search
CPC ............... G01N 33/68; G01N 33/6896; G01N 33/57484; G01N 33/57488; G01N 33/5023; G01N 2333/47; G01N 2570/00; G01N 33/564; G01N 33/57415; G16H 50/50; G16H 50/20; G16H 50/30; G16H 30/40; G16H 50/70; G16H 10/60; G16H 15/00; G16H 30/20; G16H 20/10; G16H 40/67; G06K 9/00892; G06K 9/4638; G06K 2009/366; G06K 2009/4666; G06K 9/34; G06K 9/46; G06K 9/52; G06K 9/346; G06K 9/38; G06K 9/4609; G06K 9/4619; G06K 9/6252; G06K 9/3233; G06K 9/48; G06K 9/481; G06K 9/6223; G06K 9/6273; G06K 9/6293; G06K 9/00228; G06K 9/00268; G06K 9/00288; G06K 9/6268; G06K 2009/00738; G06K 9/0014; G06K 9/00503; G06K 9/00536; G06K 9/4604; G06K 9/627; G06K 9/66; G06T 7/11; G06T 2207/10024; G06T 7/90; G06T 2207/20012; G06T 5/007; G06T 7/10; G06T 2207/20021; G06T 2207/20104; G06T 7/162; G06T 2207/20112; G06T 5/002; G06T 7/12; G06T 7/13; G06T 15/20; G06T 2210/41; G06T 7/42; G06T 7/00; G06T 2219/2016; G06T 7/60; G06T 7/70; G06T 7/73; G06T 2207/20081; G06T 9/002; G06T 11/005; G06T 2207/30004; G06T 2219/004; G06T 7/0012; G06T 7/187; G06N 5/02; G06N 99/005; G06N 7/005; G06N 5/04; G06N 20/00; G06N 3/0454; G06N 3/0436; G06N 3/084; G06N 3/088; G06N 7/00; A61K 39/0007; A61K 49/0056; C12Q 2537/165; C12Q 2600/158; C12Q 1/6883; C12Q 1/6872; C12Q 2600/156; C12Q 2600/112; C12Q 2600/118; C12Q 2600/154; C12Q 2545/101; G16B 30/00; G16B 20/00; G16B 40/00; G16B 5/00; G16B 15/00; G16B 25/00; G16B 45/00; G16B 30/10; G16B 25/10; G16B 40/20; G16B 50/00; G09F 9/00; A61B 5/7264; A61B 5/7267; A61B 6/5205
See application file for complete search history.

(56) References Cited

OTHER PUBLICATIONS

"Standard Score" Wikipedia, downloaded Mar. 26, 2018.*
T. Arai, et al. Prediction of blood culture results by measuring procalcitonin levels and other inflammatory biomarkers Am J Emergency Medicine vol. 32 (2014) p. 330-333.*
Gisslen, M et al. "Amyloid and tau cerebrospinal fluid biomarkers in HIV infection" BMC Neurology 2009 vol. 9 p. 63.*
Sunderland et al. "Decreased Beta Amyloid and increased Tau levels in cerebrospinal fluid of patients with Alzheimer disease." JAMA 2003 vol. 289 No. 10, pp. 1-10.*
White et al. "Adjustment for measurement error in evaluating diagnostic biomarkers by using an internal reliability sample" Statistics in Medicine (2013) vol. 32 pp. 4709-4725.*
Skates et al. Cancer Epidemiol. Biomarker Prev. 2007 vol. 16 No. 2 p. 334-341.*
Zou et al., Receiver-Operating Characteristic Analysis for Evaluating Diagnostic Tests and Predictive Models, Statistical Primer for Cardiovascular Research, Circulation. 2007;115:654-657, DOI: 10.1161/CIRCULATIONAHA.105.594929.

* cited by examiner

METHOD FOR CONSTRUCTING QUADRANTS WITH MULTIPLE INDEPENDENT BIOMARKERS FOR DIAGNOSING NEURODEGENERATIVE DISEASES

CROSS-REFERENCES TO RELATED APPLICATIONS

The present application claims priority to U.S. Provisional Application No. 62/188,629 filed on Jul. 4, 2015, incorporated herein by reference in its entirety.

FIELD OF THE INVENTION

The present invention relates to a method for constructing quadrants with multiple independent biomarkers for diagnosing diseases.

BACKGROUND OF THE INVENTION

Figure 1A:
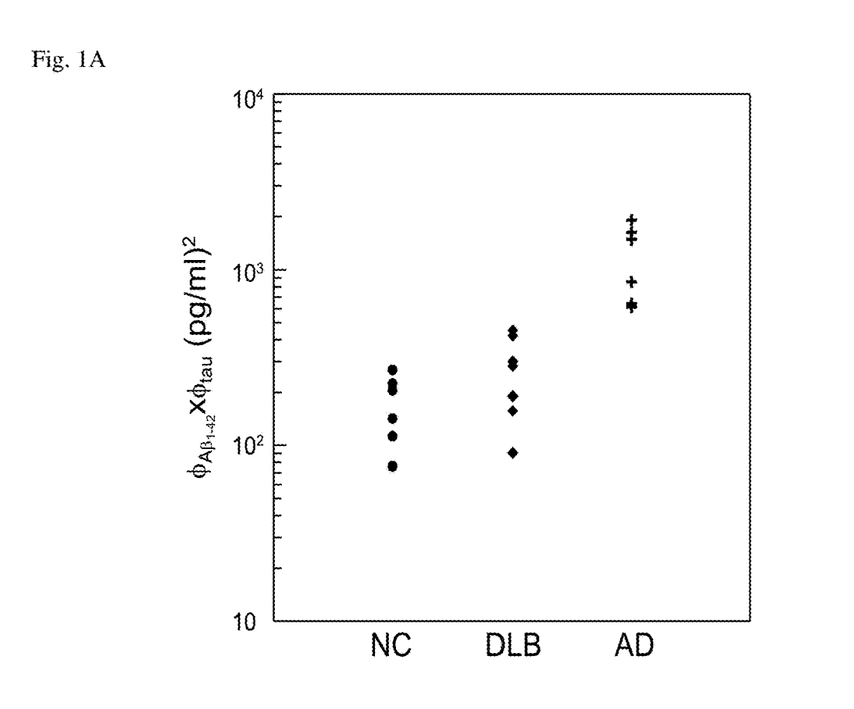
FIG. 1A: Detected concentration products of plasma $A\beta_{1-42}$ and tau protein for normal controls (NC) and patients with either dementia with Lewy Body (DLB) or Alzheimer's disease (AD).
Figure 1B:
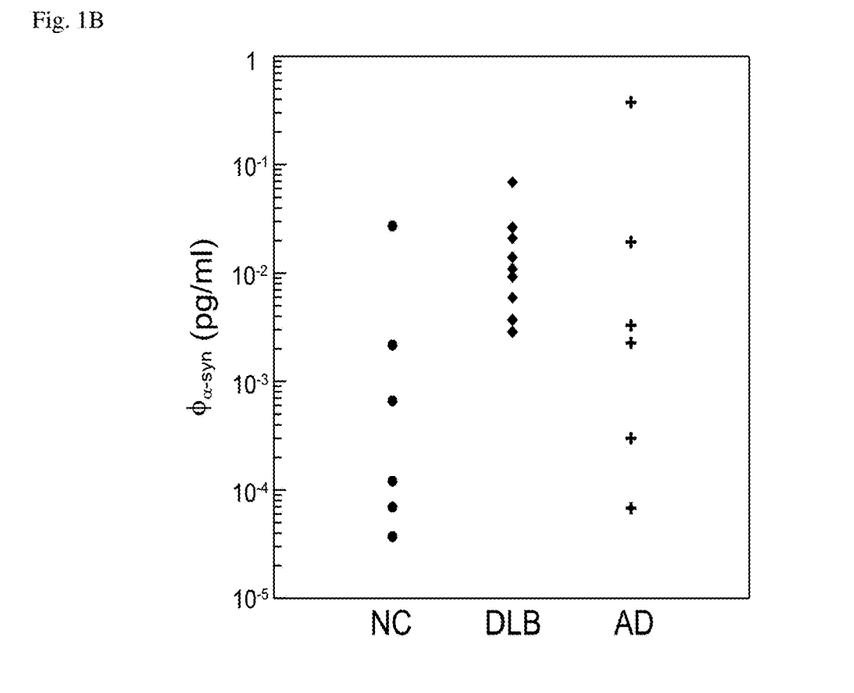
FIG. 1B: Detected concentrations of plasma α-synuclein for normal controls (NC) and patients with either dementia with Lewy Body (DLB) or Alzheimer's disease (AD).

Neurodegenerative diseases include several kinds of pathologies causing versatile diseases, such as Alzheimer's disease (AD), Parkinson's disease (PD), dementia with Lewy body (DLB), and frontotemporal dementia (FTD), etc. Due to different causes, these diseases may develop various impaired clearance of biomolecules, which are regarded as biomarkers with these diseases. For example, β-amyloid (Aβ), tau protein and their derivates are typically related to AD, while α-synuclein and its derivates are representative biomarkers for PD and DLB. It is suggested to discriminate patients by assaying the typical biomarkers. For example, AD patients show higher values for the product in concentrations of plasma $A\beta_{1-42}$ and tau protein, denoted as $\phi_{A\beta1-42} \times \phi_{tau}$, as compared to that of normal controls (NC, or referred as to healthy subjects) and DLB patients, as shown in FIG. 1A. But, in FIG. 1A, DLB patients will be missdiagnosed as normal controls. As the plasma α-synuclein is assayed for NC, DLB patients, and AD patients, patients with DLB show higher concentrations of plasma α-synuclein, denoted as $\phi_{\alpha\text{-}syn}$, as compared to NC, as shown in FIG. 1B. However, some AD patients also show the same levels of plasma α-synuclein as DLB patients. Thus, DLB patients can not be well discriminated from AD patients by merely assaying $\phi_{\alpha\text{-}syn}$. According to results in FIGS. 1A and 1B, DLB patients can not be accurately diagnosed by assaying either of plasma $\phi_{A\beta1-42} \times \phi_{tau}$ or plasma $\phi_{\alpha\text{-}syn}$.

SUMMARY OF THE INVENTION

The present invention relates to a method for constructing quadrants corresponding to different diseases in a frame of concentrations of multiple independent biomarkers, comprising:
(a) transferring original distributed concentrations of every independent biomarker to modified distributed concentrations, comprising:
 calculating the mean value and the standard deviation of the original distributed concentrations for a given independent biomarker;
 individually subtracting all the original distributed concentrations by the mean value for the given independent biomarker; and
 individually dividing all the differences by the standard deviation to get the modified distributed concentrations for the given independent biomarker;
(b) positing the modified distributed concentrations in a frame of multiple independent biomarkers; and
(c) finding a boundary optimally separating neighboring quadrants corresponding to different diseases.

DETAILED DESCRIPTION OF THE INVENTION

Figure 2:
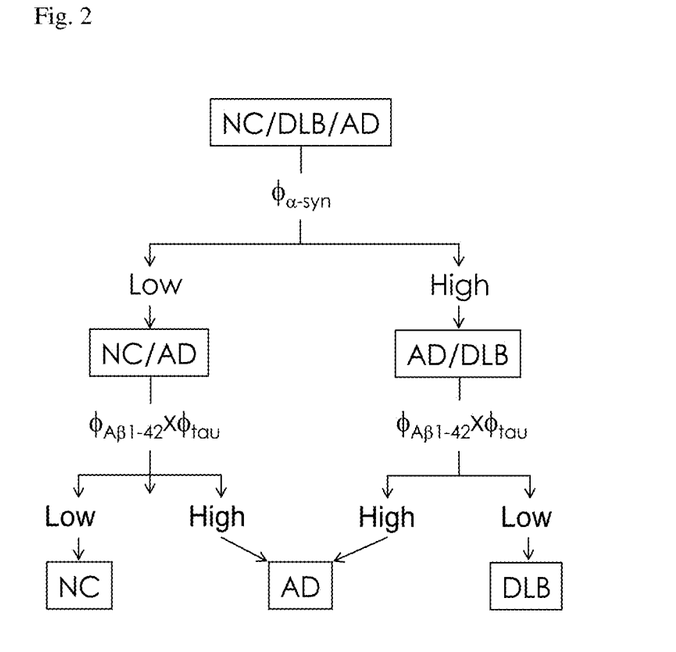
FIG. 2: A proposed flow chart to discriminate subjects belonging to NC, AD, or DLB group by assaying multiple bio-markers.

It is proposed that DLB patients can be discriminated from NC and AD, as illustrated in FIG. 2. By firstly assaying plasma α-synuclein and then assaying plasma $A\beta_{1-42}$ and tau protein, DLB patients show higher $\phi_{\alpha\text{-}syn}$ and lower $\phi_{A\beta1-42} \times \phi_{tau}$, AD patients show higher $\phi_{A\beta1-42} \times \phi_{tau}$, and NC subjects show lower $\phi_{\alpha\text{-}syn}$ and lower $\phi_{A\beta1-42} \times \phi_{tau}$. The illustration in FIG. 2 reveals the possibility to achieve high clinical sensitivity and specificity in discriminating patients with DLB or other neurodegenerative diseases such as AD, PD, and FTD by assaying multiple biomarkers.

Therefore, the present invention is to investigate a method for discriminating patients with different diseases by assaying multiple biomarkers.

The present invention provides a method for constructing quadrants corresponding to different diseases in a frame of concentrations of multiple independent biomarkers, comprising:

(a) transferring original distributed concentrations of every independent biomarker to modified distributed concentrations, comprising:
  calculating the mean value and the standard deviation of the original distributed concentrations for a given independent biomarker;
  individually subtracting all the original distributed concentrations by the mean value for the given independent biomarker; and
  individually dividing all the differences by the standard deviation to get the modified distributed concentrations for the given independent biomarker;
(b) positing the modified distributed concentrations in a frame of multiple independent biomarkers; and
(c) finding a boundary optimally separating neighboring quadrants corresponding to different diseases.

In an embodiment, the original distributed concentrations are either originally detected concentrations or transferred concentrations of the originally detected concentrations via mathematic calculation. The mathematic calculation may be, but not limited to, logarithm, trigonometric function, sigmoid function, or any combinations thereof.

In an embodiment, the independent biomarker may be either a single kind of bio-molecule or a combination of several kinds of bio-molecules. The independent biomarker may exist in, but not limited to, blood, urine, cerebrospinal fluid, or saliva.

In an embodiment, the number of the multiple independent biomarkers is more than one.

In an embodiment, the method for finding a boundary optimally separating neighboring quadrants corresponding to different diseases in step (c) is ROC curve analysis.

In an embodiment, the independent biomarkers may be, but not limited to, plasma α-synuclein, β-amyloid, tau protein, and their derivatives to construct quadrants corresponding to healthy subjects and patients with neurodegenerative disease. The neurodegenerative disease may be, but not limited to, dementia with Lewy body, Parkinson's disease, Alzheimer's disease, or frontotemporal dementia.

EXAMPLES

The examples below are non-limiting and are merely representative of various aspects and features of the present invention. Therefore, the method of the present invention should not be limited to only for diagnosing neurodegenerative disease.

Example 1

Subjects

Subjects including normal controls (n=6), DLB patients (n=9), AD patients (n=6), PD patients (n=9), and FTD patients (n=6) were enrolled. The ages of all subjects were from 47 to 87 years. The demographic information of subjects was listed in Table 1. The subjects were divided into disease groups according to neuropsychological tests and clinical symptoms. Some subjects were examined with magnetic resonance imaging. There was no combination of these diseases for any one of subjects. The plasma biomarkers $Aβ_{1-42}$, tau protein, and α-synuclein were assayed for each subject by using immunomagnetic reduction (Yang, C. C., Yang, S. Y., Chieh, J. J., Horng, H. E., Hong, C. Y., Yang, H. C., Chen, K. H., Shih, B. Y., Chen, T. F., Chiu, M. J. (2011) Biofunctionalized magnetic nanoparticles for specifically detecting biomarkers of Alzheimer's disease in vitro. ACS Chem. Neurosci. 2, 500-505; Chiu, M. J., Yang, S. Y., Chen, T. F., Chieh, J. J., Huang, T. Z., Yip, P. K., Yang, H. C., Cheng, T. W., Chen, Y. F., Hua, M. S., and Horng, H. E. (2012) New assay for old markers-plasma beta amyloid of mild cognitive impairment and Alzheimer's disease. Curr. Alzheimer Res. 9, 1142-1147; Yang, S. Y., Chieh, J. J., Yang, C. C., Liao, S. H., Chen, H. H., Horng, H. E., Yang, H. C., Hong, C. Y., Chiu, M. J., Chen, T. F., Huang, K. W., and Wu, C. C. (2013) Clinic applications in assaying ultra-low-concentration bio-markers using HTS SQUID-based AC magnetosusceptometer. IEEE Trans. Appl. Supercond. 23, 1600604-1600607; Chiu, M. J., Chen, Y. F., Chen, T. F., Yang, S. Y., Yang, F. P. Gloria, Tseng, T. W., Chieh, J. J., Chen, J. C. Rare, Tzen, K. Y., Hua, M. S., and Horng, H. E. (2013) Plasma tau as a window to the brain-negative associations with brain volume and memory function in mild cognitive impairment and early alzheimer's disease. Human Barin Mapping, 35, 3132-3142; Tzen, K. Y., Yang, S. Y., Chen, T. F., Cheng, T. W., Horng, H. E., Wen, H. P., Huang, Y. Y., Shiue, C. Y., and Chiu, M. J. (2014) Plasma Aβ but not tau related to brain PiB retention in early Alzheimer's disease. ACS Neuro. Chem. 5, 830 (2014)).

TABLE 1

Demographic information of enrolled subjects.

| Group | Numbers (Male/Female) | Age (years) |
|---|---|---|
| NC | 6 (2/4) | 53-73 |
| DLB | 9 (6/3) | 65-81 |
| AD | 6 (3/3) | 65-87 |
| PD | 9 (5/4) | 65-81 |
| FTD | 6 (0/6) | 47-73 |

NC: normal control,
DLB: dementia with Lewy Body
AD: Alzheimer's disease,
PD: Parkinson's disease,
FTD: frontotemporal disease Assay Results The detected concentrations of $Aβ_{1-42}$, tau protein, and α-synuclein in plasma for all the subjects were shown in FIGS. 3A-3C. The detected concentrations of $Aβ_{1-42}$, tau protein, and α-synuclein in plasma were denoted as $φ_{Aβ1-42}$, $φ_{tau}$, $φ_{α-syn}$, respectively.

Figure 3A:
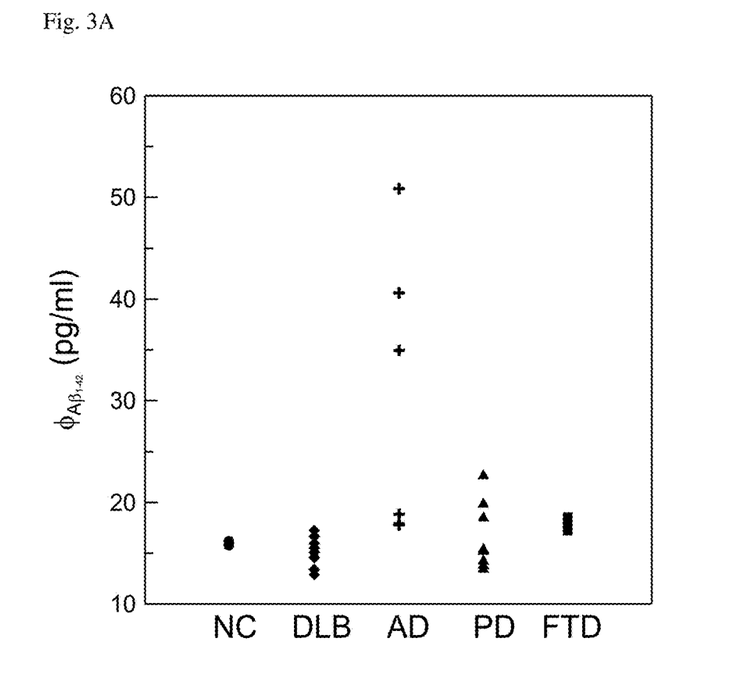
FIG. 3A: Detected concentrations of $A\beta_{1-42}$ in plasma with variously neurodegenerative diseases.

In FIG. 3A, almost all the detected concentrations of plasma $Aβ_{1-42}$ were below 20 pg/ml, except some data points with AD and PD. It was not easy to discriminate patients with various diseases according to the concentration of plasma $Aβ_{1-42}$. As to the detected concentration of plasma tau protein in FIG. 3B, NC showed relatively low concentrations of plasma tau protein, while AD and FTD showed relatively high concentrations. In case, it was not significant to differentiate DLB from PD, as well as AD from FTD. In FIG. 3C, PD could be obviously recognized due to the highest level for the concentrations of plasma α-synuclein as compared to other groups. DLB showed the second highest level for the concentrations of plasma α-synuclein. FTD was clearly recognized because of the definitely lowest level for the concentrations of plasma α-synuclein. However, the plasma α-synuclein for NC and AD distributed the same concentration range. It failed to discriminate NC and AD by using the concentration of plasma α-synuclein.

Figure 3B:
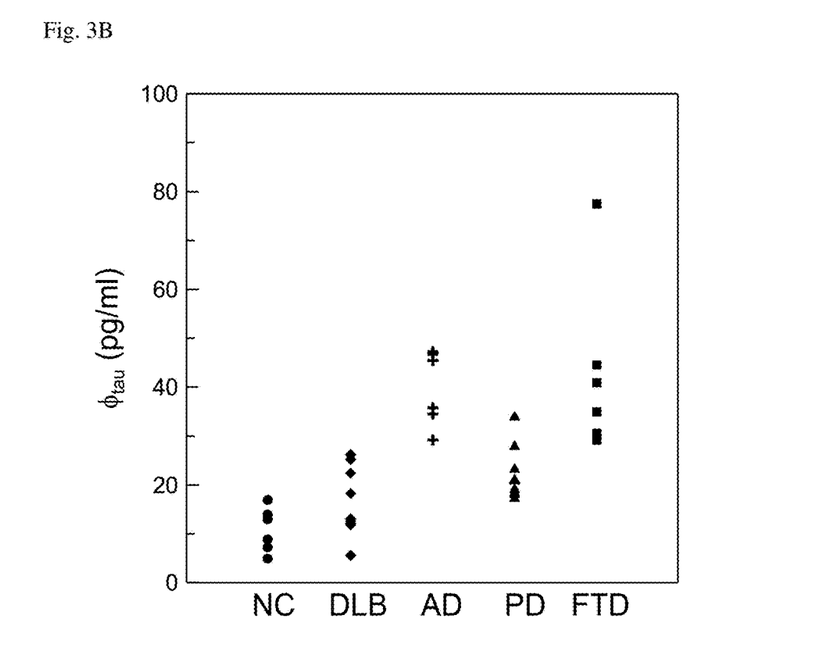
FIG. 3B: Detected concentrations of tau protein in plasma with variously neurodegenerative diseases.
Figure 3C:
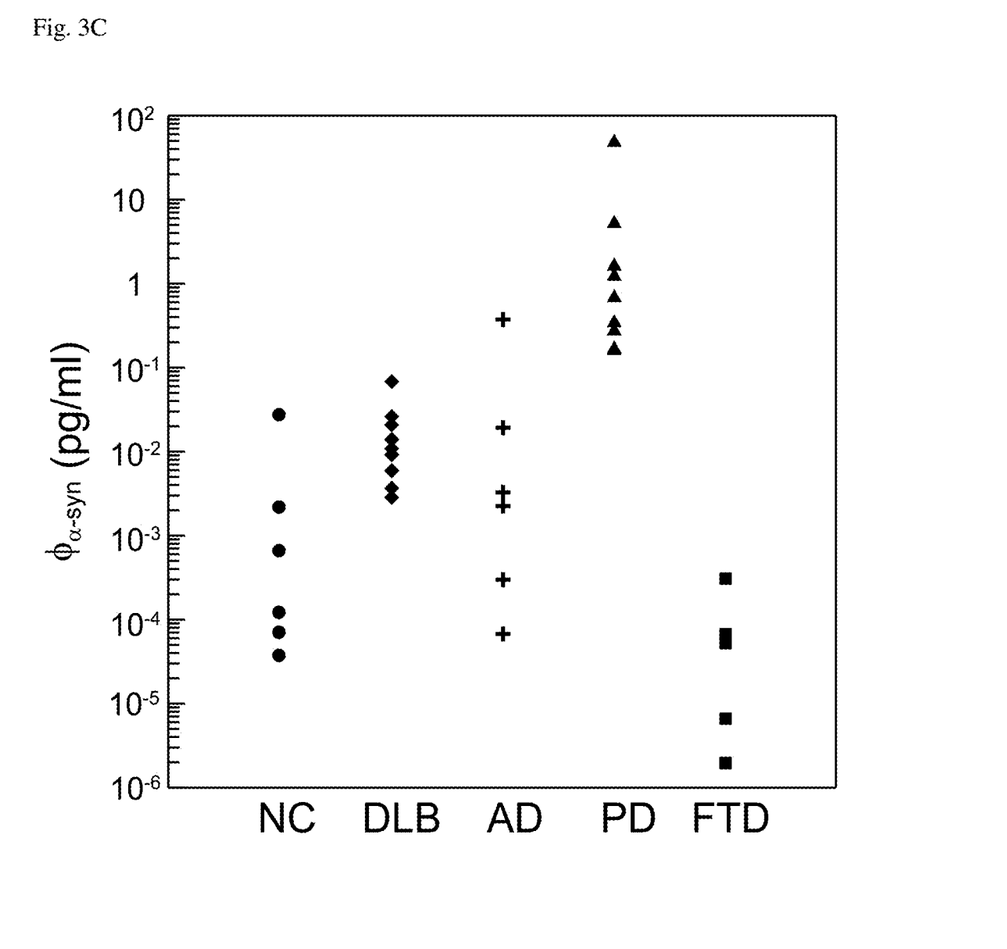
FIG. 3C: Detected concentrations of α-synuclein in plasma with variously neurodegenerative diseases.

The results in FIGS. 3A-3C revealed the fact similar to that in FIGS. 1A and 1B that it failed to differentiate patients with various diseases by using single bio-marker. Multiple bio-markers were necessarily developed to achieve high discrimination among diseases.

Multiple Bio-Markers

Figure 4:
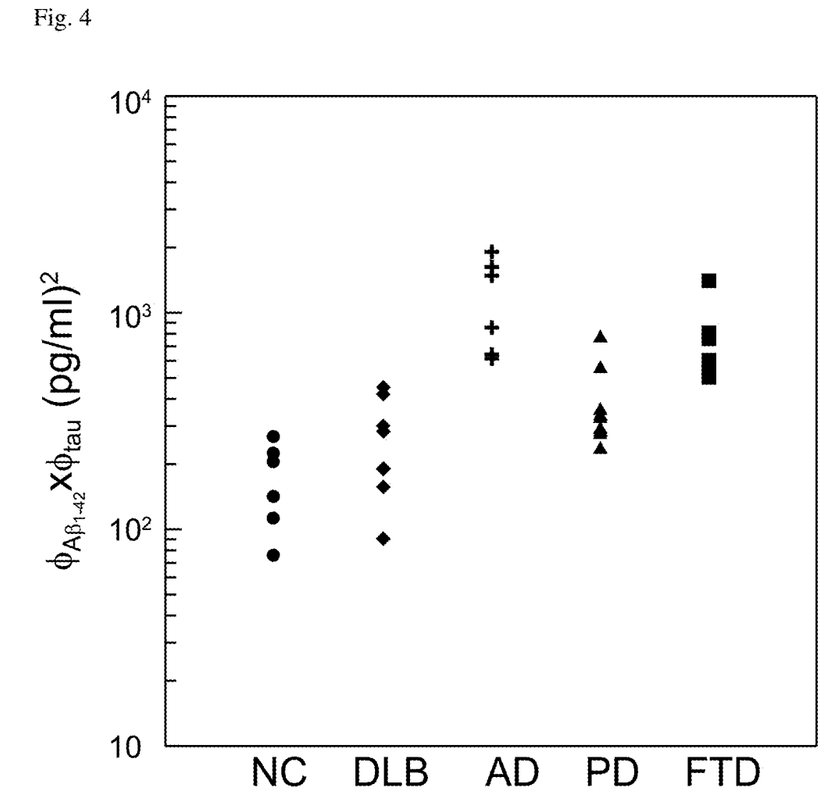
FIG. 4: Product in concentrations of plasma $A\beta_{1-42}$ and tau protein for all subjects.

It had been reported that the product in concentrations, denoted as $\phi_{A\beta1-42} \times \phi_{tau}$, of plasma $A\beta_{1-42}$ and tau protein was superior to either of plasma $A\beta_{1-42}$ or plasma tau protein for diagnosing neurodegenerative disease, especially AD. The $\phi_{A\beta1-42} \times \phi_{tau}$ for all subjects were plotted in FIG. 4. The AD and FTD patients showed higher values for $\phi_{A\beta1-42} \times \phi_{tau}$ as compared to NC, DLB, and PD. With the results in FIG. 3C, FTD patients showed the lowest level for the concentrations of plasma α-synuclein. Thus, it was able to differentiate FTD from AD by additionally assaying plasma α-synuclein after finding $\phi_{A\beta1-42} \times \phi_{tau}$.

For the groups with lower values of $\phi_{A\beta1-42} \times \phi_{tau}$, i.e. NC, DLB, and PD, they showed different levels of $\phi_{\alpha-syn}$, as shown in FIG. 3C. PD patients showed the highest level of $\phi_{\alpha-syn}$, while NC subjects showed the lowest level of $\phi_{\alpha-syn}$. Hence, it was able to discriminate PD, DLB, and NC by additionally assaying plasma α-synuclein after finding $\phi_{A\beta1-42} \times \phi_{tau}$. In summary, a flow chart for discriminating subjects of NC, DLB, AD, PD, and FTD by assaying plasma $A\beta_{1-42}$, tau protein, and α-synuclein was proposed and shown in FIG. 5.

2D Map for Disease Discrimination

Figure 5:
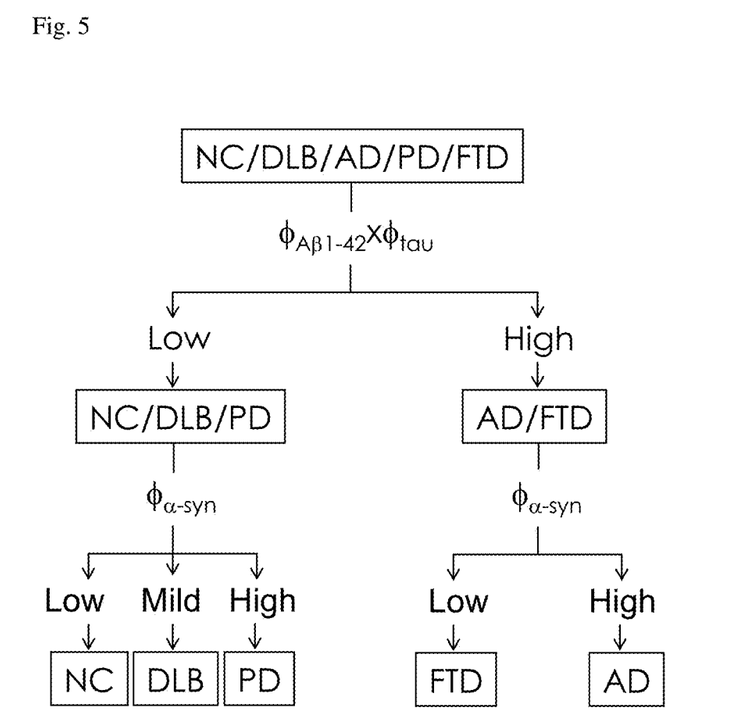
FIG. 5: A proposed flow chart to discriminate subjects in various disease groups by assaying multiple bio-markers.
Figure 6:
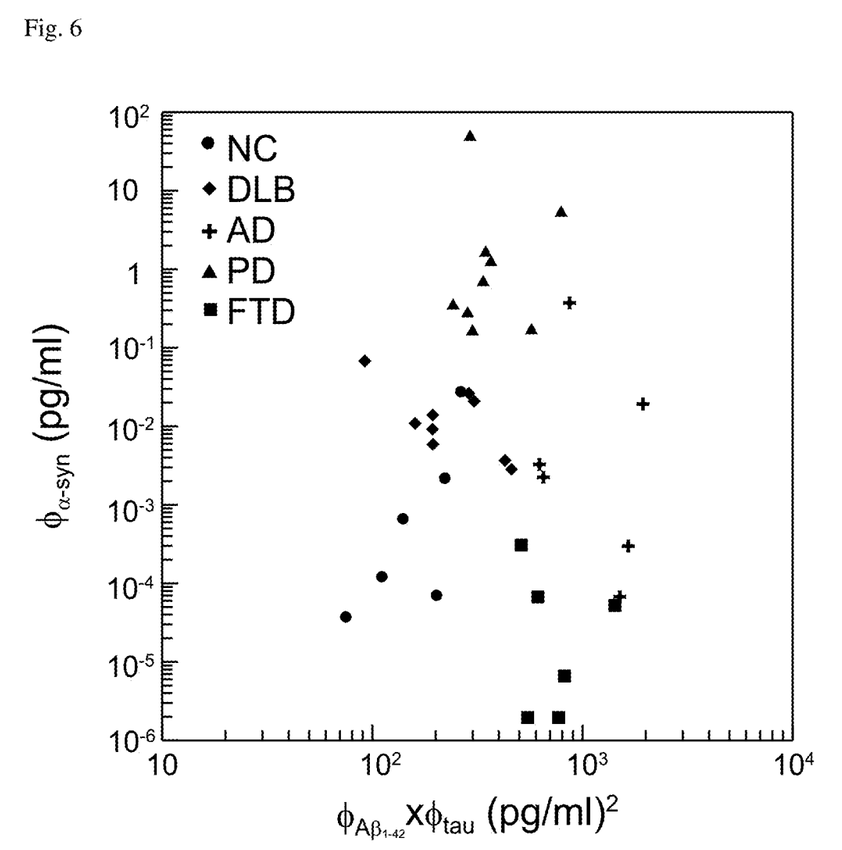
FIG. 6: Detected values in the frame of plasma $\phi_{A\beta1-42} \times \phi_{tau}$ and plasma $\phi_{\alpha\text{-}syn}$ for all subjects.
Figure 7:
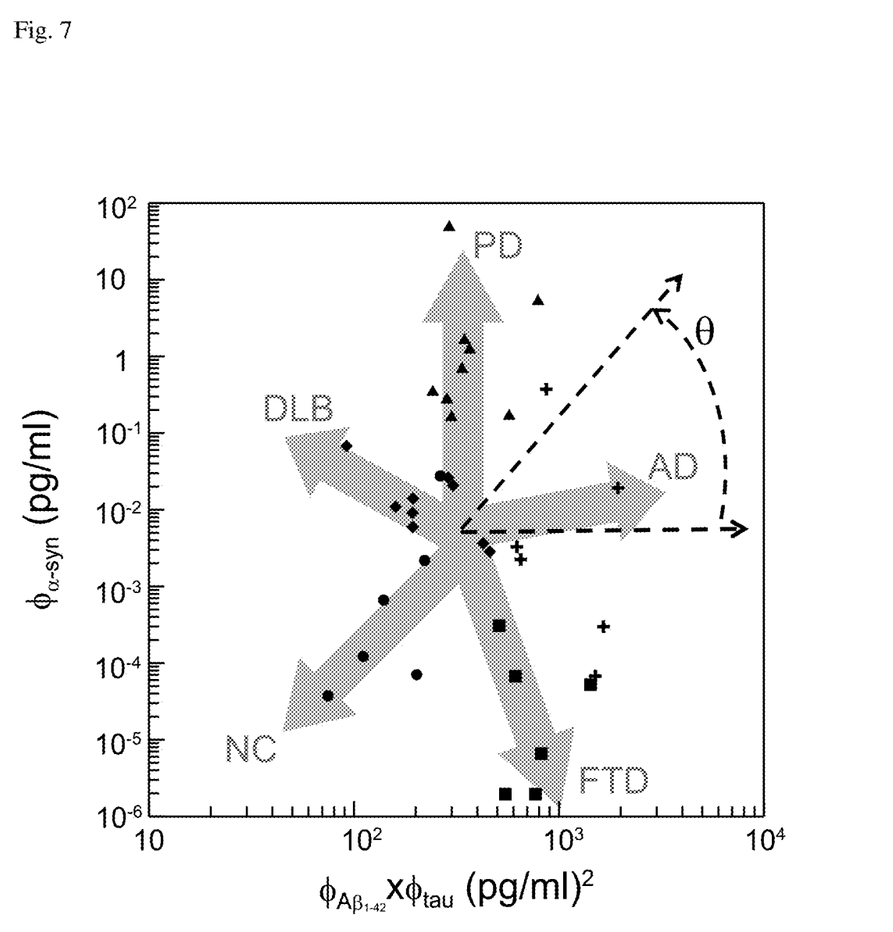
FIG. 7: Illustration of the polar angle θ to discriminate disease groups in the frame of plasma $\phi_{A\beta1-42} \times \phi_{tau}$ and plasma $\phi_{\alpha\text{-}syn}$ for all subjects.

According to FIG. 5, plasma $\phi_{A\beta1-42} \times \phi_{tau}$ and plasma $\phi_{\alpha-syn}$ could be used as diagnostic parameters for discriminating NC, DLB, AD, PD, and FTD. It provided a motivation to construct the two-dimensional distribution in the frame of plasma $\phi_{A\beta1-42} \times \phi_{tau}$ and plasma $\phi_{\alpha-syn}$, as shown in FIG. 6. In FIG. 6, the data points for various groups were distributed in various region. Roughly speaking, standing at the center of the region occupied with the data points, NC was distributed in the lower-left region, FTD was distributed in the lower-right region, AD was roughly in the right region, PD was distributed in the upper region, and DLB was distributed in the upper-left region. It seemed possible to use a polar angle θ as a parameter to discriminate subjects into various disease groups, as illustrated in FIG. 7.

The polar angle θ was the angle span by a ray with respect to the horizontal ray. The horizontal ray was not the x axis in the frame of plasma $\phi_{A\beta1-42} \times \phi_{tau}$ and plasma $\phi_{\alpha-syn}$, but started from the center of the region occupied with the data points. It was necessary to find the starting point of the horizontal ray. The coordinates of the starting point of the horizontal ray could be defined as the averaged values of $\phi_{A\beta1-42} \times \phi_{tau}$ and $\phi_{\alpha-syn}$ of all subjects. However, the detected values of $\phi_{A\beta1-42} \times \phi_{tau}$ or $\phi_{\alpha-syn}$ distributed over several orders of magnitude. Points with higher values would be more weighted when calculating the average value of all points. This was the reason why FIG. 6 or FIG. 7 was not plotted in the linear-to-linear scale. Instead, FIG. 6 and FIG. 7 were plotted in the log-to-log scale.

Figure 8:
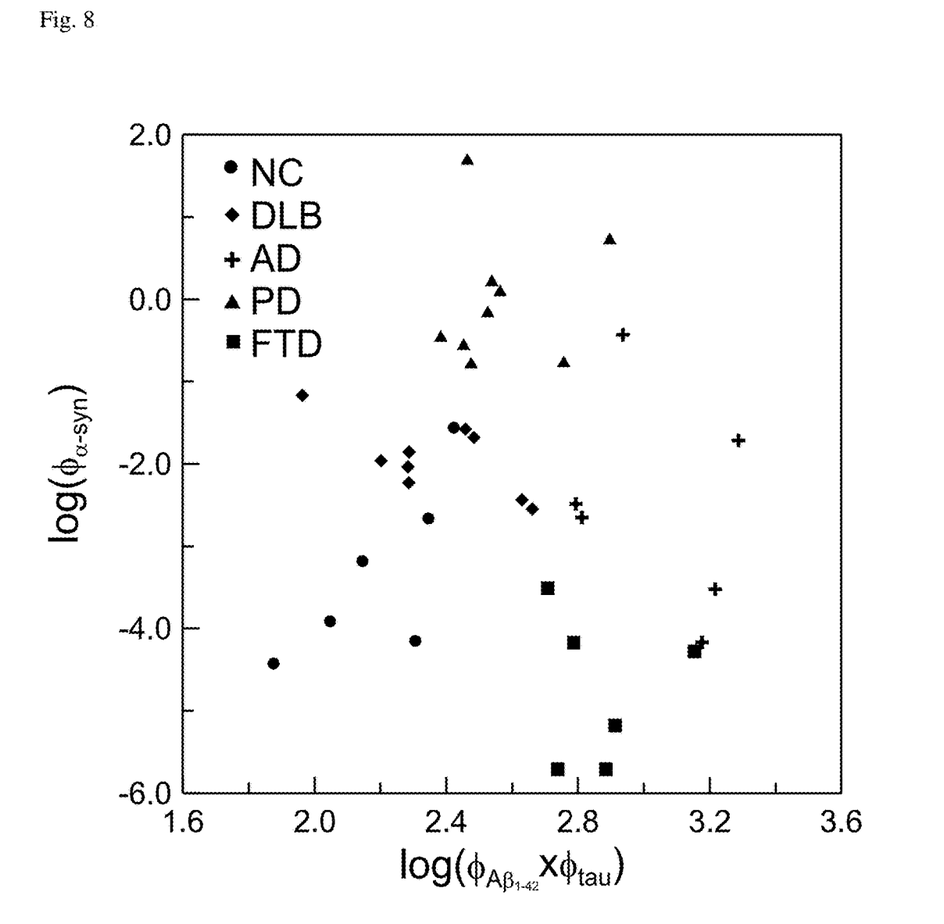
FIG. 8: Distribution of original concentrations, $\log(\phi_{\alpha\text{-}syn})$ and $\log(\phi_{A\beta1-42} \times \phi_{tau})$ for variously disease groups.

The detected values of all points in FIG. 6 were transferred via logarithm. The $\log(\phi_{\alpha-syn})$ versus $\log(\phi_{A\beta1-42} \times \phi_{tau})$ were plotted in FIG. 8. Hereafter, the values of $\log(\phi_{\alpha-syn})$ and $\log(\phi_{A\beta1-42} \times \phi_{tau})$ were referred as to original concentrations. It was found that the values of all $\log(\phi_{\alpha-syn})$'s or all $\log(\phi_{A\beta1-42} \times \phi_{tau})$'s were distributed at the same order of magnitude. For example, $\log(\phi_{\alpha-syn})$'s were within the range from −6 to 2, and $\log(\phi_{A\beta1-42} \times \phi_{tau})$'s were within the range from 1.6 to 3.6. Now, each data point was equally weighted when calculating their averaged values of $\log(\phi_{\alpha-syn})$'s and $\log(\phi_{A\beta1-42} \times \phi_{tau})$'s. In addition, the standard deviations of all $\log(\phi_{\alpha-syn})$'s and all $\log(\phi_{A\beta1-42} \times \phi_{tau})$'s were calculated. Then, each $\log(\phi_{\alpha-syn})$ and $\log(\phi_{A\beta1-42} \times \phi_{tau})$ were transferred via the following equations:

$$\phi'_{A\beta1-42 \times tau} = [\log(\phi_{A\beta1-42} \times \phi_{tau}) - M_{\log(\phi_{A\beta1-42} \times \phi_{tau})}] / SD_{\log(\phi_{A\beta1-42} \times \phi_{tau})}, \quad \text{(Eq. 1)}$$

$$\phi'_{\alpha-syn} = [\log(\phi_{\alpha-syn}) - M_{\log(\phi_{\alpha-syn})}] / SD_{\log(\phi_{\alpha-syn})}, \quad \text{(Eq. 2)}$$

Where $M_{\log(\phi_{A\beta1-42} \times \phi_{tau})}$ and $SD_{\log(\phi_{A\beta1-42} \times \phi_{tau})}$ denoted the averaged value and standard deviation of all $\log(\phi_{A\beta1-42} \times \phi_{tau})$'s, $M_{\log(\phi_{\alpha-syn})}$ and $SD_{\log(\phi_{\alpha-syn})}$ denoted the averaged value and standard deviation of all $\log(\phi_{\alpha-syn})$'s. The $\phi'_{A\beta1-42 \times tau}$ and $\phi'_{\alpha-syn}$, which were referred as to modulated concentrations, were plotted in FIG. 9.

The origin in the frame of $\phi'_{\alpha-syn}$ and $\phi'_{A\beta1-42 \times tau}$ was the starting point of the horizontal ray in FIG. 7. That was, the horizontal ray was the x axis of FIG. 9.

Polar Angle for Disease Discrimination

Figure 9:
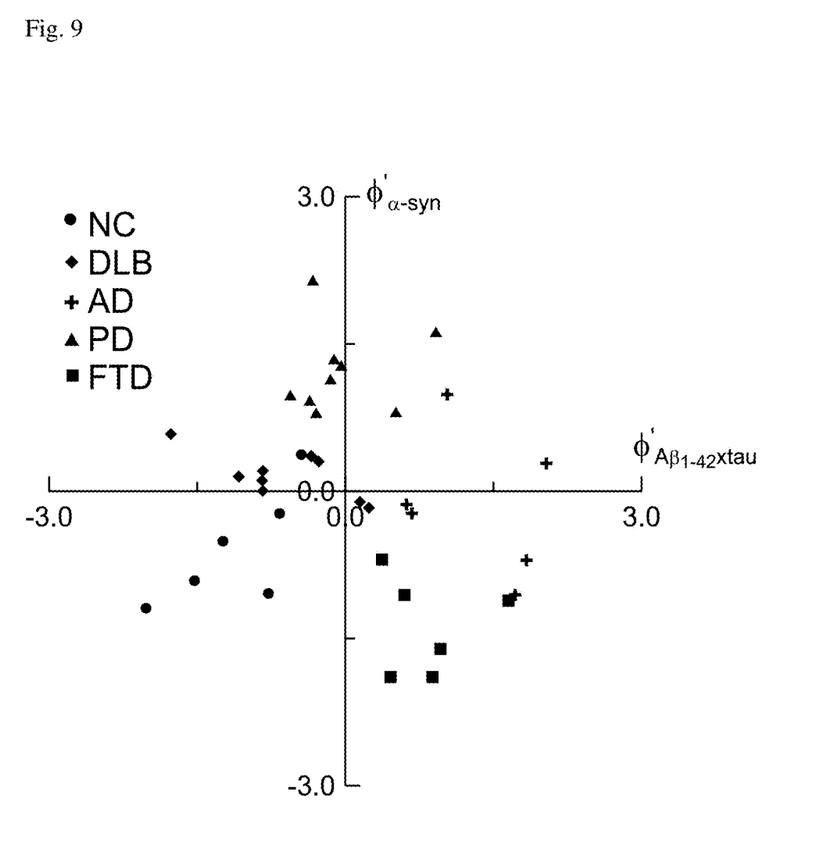
FIG. 9: Distribution of modulated concentrations in the frame of $\phi'_{\alpha\text{-}syn}$ and $\phi'_{A\beta1-42} \times \phi_{tau}$ for variously disease groups.

In FIG. 9, there existed a boundary which optimally separated subjects in two disease groups locating in neighboring regions. The boundary could be determined by suitably constructing a ray along a certain polar angle θ' from the origin in the frame of $\phi'_{\alpha-syn}$ and $\phi'_{A\beta1-42 \times tau}$. An example to construct boundary optimally separating NC and DLB was given. Other boundaries for optimally separating two neighboring groups in FIG. 9 can be constructed by following the same processes.

Firstly, each point of NC group and DLB group was assigned with a polar angle θ'. For a given point i with the coordinate ($\phi'_{A\beta1-42 \times tau,i}$, $\phi'_{\alpha-syn,i}$) in FIG. 9, the polar angle $\theta'_i$ was obtained via $$\theta'_i = \tan^{-1}(\phi'_{\alpha-syn,i} / \phi'_{A\beta1-42 \times tau,i})$$

Among the points in NC and DLB groups, there existed a minimum polar angle, referred as $\theta'_{min}$. Every $\theta'_i$ was subtracted with $\theta'_{min}$ to get the shifted polar angle $\theta'_{s,i}$, i.e.

$$\theta'_{s,i} = \theta'_i - \theta'_{min}$$

Figure 10:
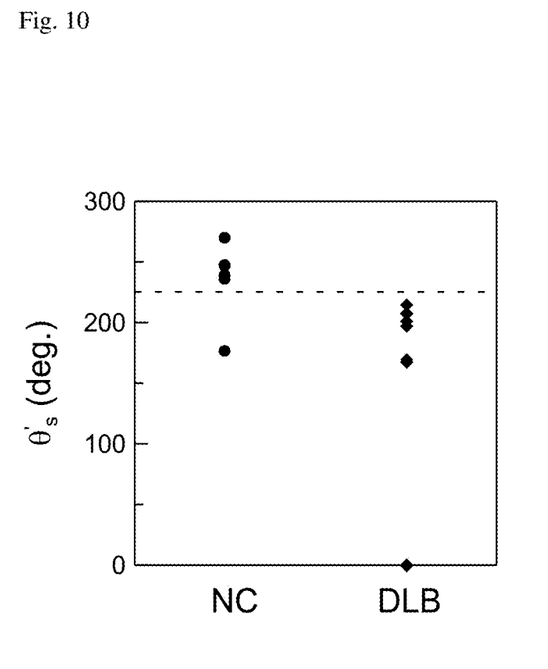
FIG. 10: Shifted polar angles $\theta'_s$ for NC group and DLB group in FIG. 9.
Figure 11:
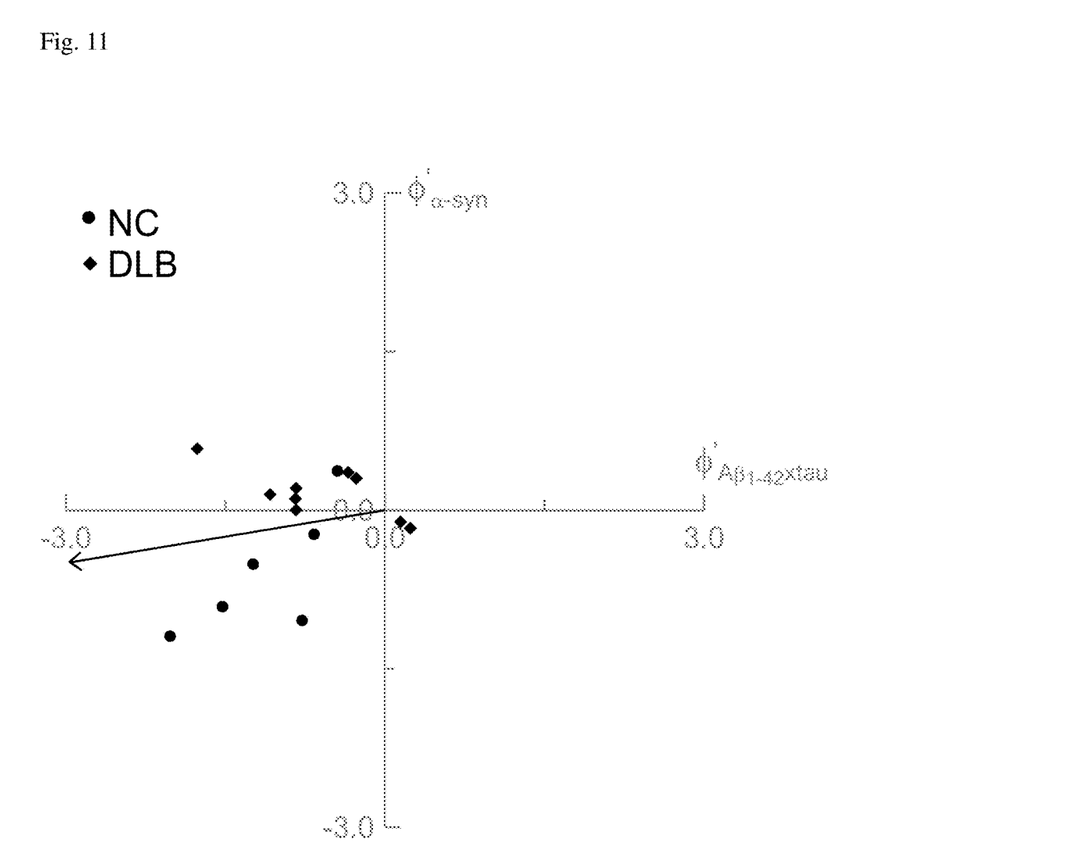
FIG. 11: Boundary guided with the ray along the polar angle 189.48° optimally discriminating NC and DLB subjects.

The $\theta'_s$'s for points belonging to NC and DLB groups in FIG. 9 were plotted in FIG. 10. Through the analysis of receiver operating characteristic (ROC) curve, the cut-off value of $\theta'_s$ to optimally discriminate NC and DLB subjects was found to be 225.28°, as plotted with a dashed line in FIG. 10. The corresponding sensitivity and specificity were 0.833 and 1.000. By adding $\theta'_{min}$ to 225.28°, the polar angle optimally discriminating NC and DLB groups in FIG. 9 was 189.48°. The ray along the polar angle 189.48° was plotted with the solid line in FIG. 11.

Figure 12:
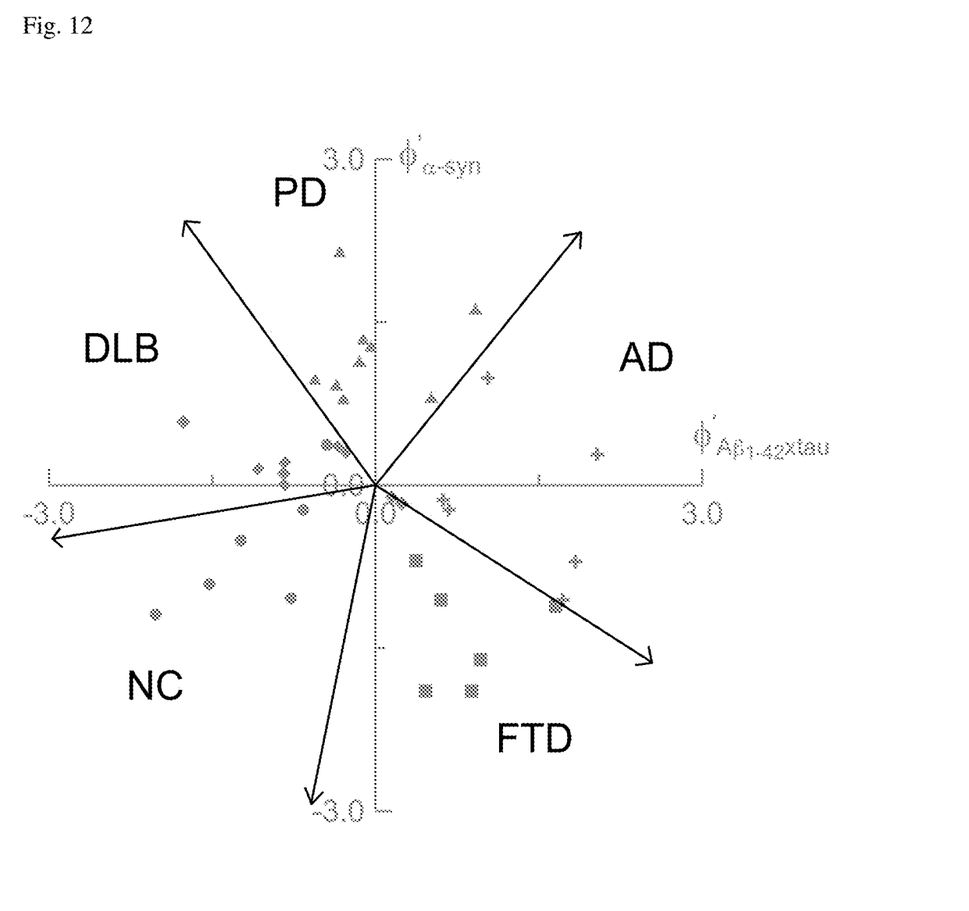
FIG. 12: Boundaries denoted with rays along specific polar angles to optimally discriminating subjects with NC (•), DLB (♦), PD (▲), AD (+), or FTD (■).

The boundaries optimally separating neighboring groups in FIG. 9 could be found, as plotted with solid lines in FIG. 12.

Utilization of 2D Map for Disease Diagnosis

With the boundaries in FIG. 12, the two-dimensional map in the frame of $\phi'_{\alpha-syn}$ and $\phi'_{A\beta1-42 \times tau}$ were divided into several quadrants. Each quadrant corresponded to one kind of diseases. Once the concentrations of plasma $A\beta_{1-42}$, tau protein, and α-synuclein of a subject had been detected, the modulated concentrations could be obtained via Eqs. (1) and (2). Then, the position of modulated concentrations with this subject could be found in FIG. 12. The subject could be accurately diagnosed.

One skilled in the art readily appreciates that the present invention is well adapted to carry out the objects and obtain the ends and advantages mentioned, as well as those inherent therein. The biomarkers and uses thereof are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations, which are not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A method for discriminating a plurality of neurodegenerative diseases by constructing quadrants corresponding to the plurality of neurodegenerative diseases in a frame of concentrations of multiple independent biomarkers, comprising:
    (a) transferring values of original distributed concentrations of every independent biomarker to values of modified distributed concentrations, comprising:
        calculating the mean value and the standard deviation of the values of original distributed concentrations for a given independent biomarker;
        individually subtracting the values of original distributed concentrations by the mean value for each of the given independent biomarker; and
        individually dividing all the differences by the standard deviation to get the values of modified distributed concentrations for each of the given independent biomarker;
    (b) creating the frame of concentrations of multiple independent biomarkers and positing the values of the modified distributed concentrations in the frame, and
    (c) separating the values of the modified distributed concentrations which are corresponding to the plurality of neurodegenerative diseases with a boundary optimally separating each of the plurality of neurodegenerative diseases in the frame so as to discriminate the plurality of neurodegenerative diseases;
    wherein the plurality of neurodegenerative diseases comprises dementia with Lewy body, Parkinson's disease, Alzheimer's disease, and frontotemporal dementia, and the independent biomarkers are selected from the group consisting of plasma α-synuclein, β-amyloid and tau protein.

2. The method of claim 1, wherein the original distributed concentrations are originally detected concentrations or the originally detected concentrations transformed via mathematic calculation.

3. The method of claim 1, wherein the independent biomarkers are obtained from blood, urine, cerebrospinal fluid, or saliva.

4. The method of claim 1, wherein the number of the multiple independent biomarkers is more than one.

5. The method of claim 1, wherein the boundary optimally separating each of the plurality of neurodegenrative diseases is obtained using ROC curve analysis.

6. The method of claim 1, wherein the values of original distributed concentrations of every independent biomarker is transferred to values of modified distributed concentrations via the following equations:

$$\phi'_{A\beta1\text{-}42\times tau}=[\log(\phi_{A\beta1\text{-}42}\times\phi_{tau})-M_{\log(\phi_{A\beta1\text{-}42}\times\phi_{tau})}]/\text{SD}_{\log(\phi_{A\beta1\text{-}42}\times\phi_{tau})}, \quad \text{(Eq. 1)}$$

$$\phi'_{\alpha\text{-}syn}=[\log(\phi_{\alpha\text{-}syn})-M_{\log(\phi_{\alpha\text{-}syn})}]/\text{SD}_{\log(\phi_{\alpha\text{-}syn})}, \quad \text{(Eq. 2)}.$$

* * * * *